Figure 1:
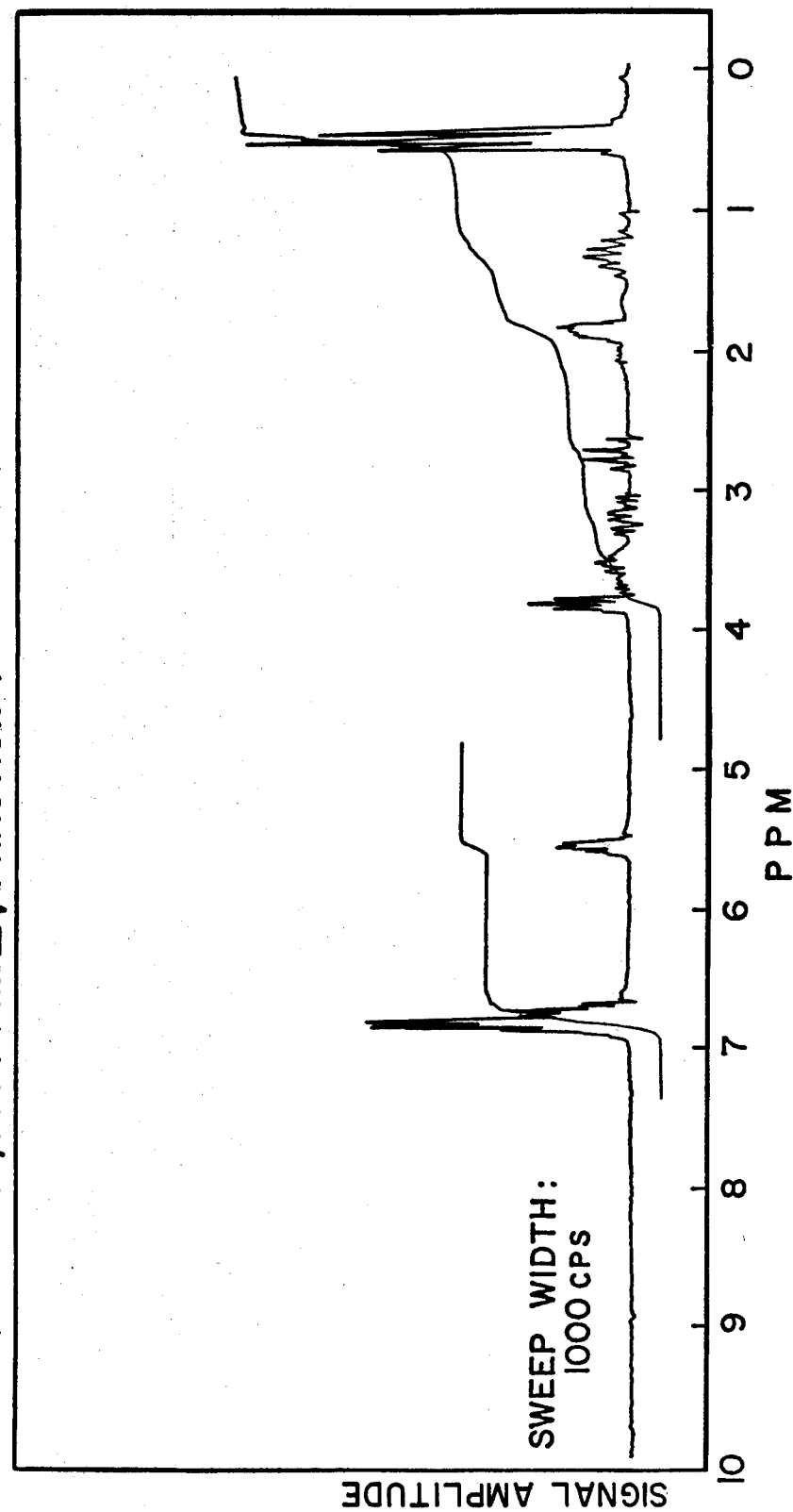

United States Patent [19]

Vinals et al.

[11] 4,115,406
[45] Sep. 19, 1978

[54] 2-ALKYL-4-PHENYL-DIHYDROPYRANS AND PROCESSES FOR AUGMENTING THE ORGANOLEPTIC PROPERTIES OF FOODSTUFFS AND TOBACCO USING ONE OR MORE OF SAID PYRANS

[75] Inventors: Joaquin Francisco Vinals, Red Bank, N.J.; Jacob Kiwala, Brooklyn, N.Y.; Denis E. Hruza, Sr., Brick Town, N.J.; John B. Hall, Rumson, N.J.; Manfred Hugo Vock, Locust, N.J.

[73] Assignee: International Flavors & Fragrances Inc., New York, N.Y.

[21] Appl. No.: 847,094

[22] Filed: Oct. 31, 1977

Related U.S. Application Data

[62] Division of Ser. No. 780,684, Mar. 23, 1977, Pat. No. 4,071,535, which is a division of Ser. No. 676,389, Apr. 12, 1976, Pat. No. 4,071,034.

[51] Int. Cl.[2] .......................................... C07D 309/04
[52] U.S. Cl. .................................................. 260/345.1
[58] Field of Search ...................................... 260/345.1

[56] References Cited
PUBLICATIONS
Williams et al., JACS, 72, 5738 (1950).

*Primary Examiner*—Nicky Chan
*Attorney, Agent, or Firm*—Arthur L. Liberman; Harold Haidt; Franklin D. Wolffe

[57] ABSTRACT

Described is the novel compound group, 2-alkyl-4-phenyl-dihydropyrans having the generic structure:

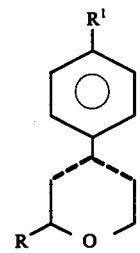

where one of the dashed lines is a carbon-carbon double bond and the other of the dashed lines is a carbon-carbon single bond, $R^1$ is one of $C_1$–$C_3$ alkyl, and R is one of $C_2$–$C_4$ alkyl, a process for producing same; a process comprising adding to tobacco an amount sufficient to augment the flavor or aroma of such tobacco of one or more of said pyran compounds; flavor formulations for use in conjunction with tobacco products containing one or more of such pyrans; a process comprising adding to foodstuffs, foodstuff flavorings, chewing gums, chewing gum flavorings, toothpaste and toothpaste flavorings one or more of said pyran compounds in a quantity sufficient to augment or enhance neroli-like and grape-like flavors, and flavoring compositions containing said pyran compounds.

1 Claim, 4 Drawing Figures

IR SPECTRUM, EXAMPLE I, FRACTION 7

NMR SPECTRUM: EXAMPLE II, FRACTION 7

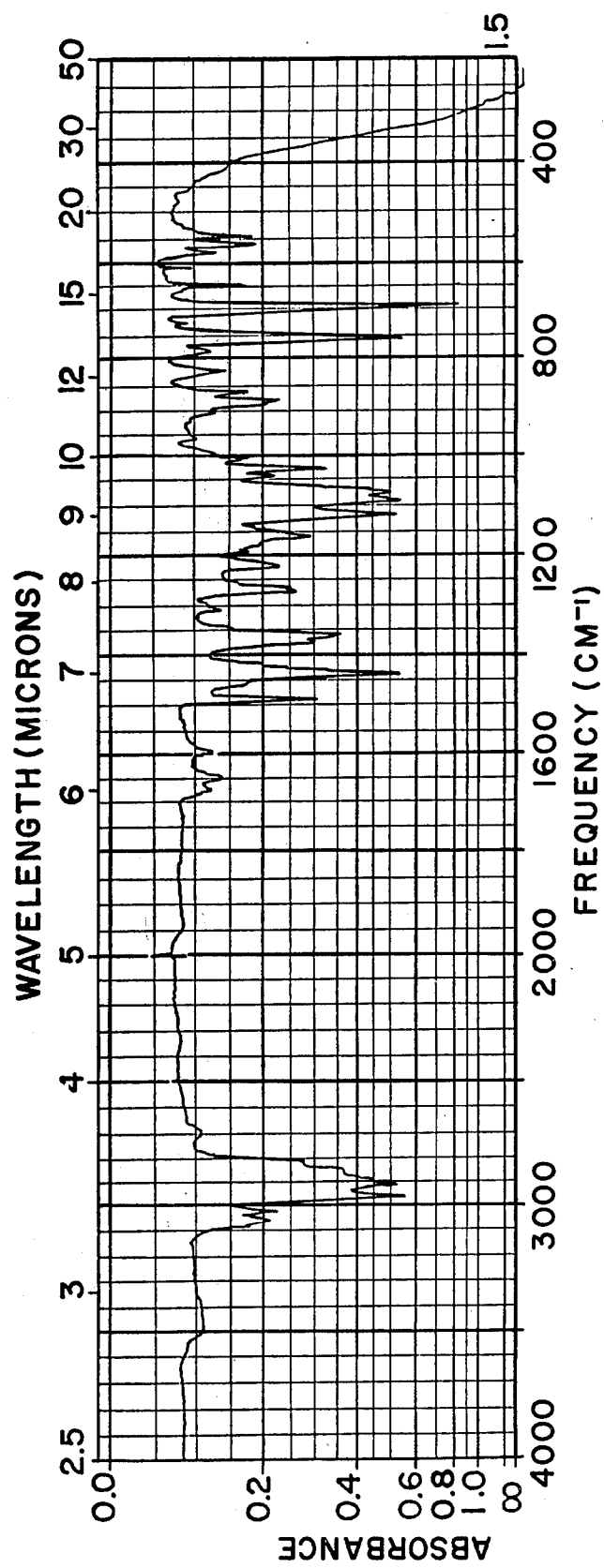

2-ALKYL-4-PHENYL-DIHYDROPYRANS AND PROCESSES FOR AUGMENTING THE ORGANOLEPTIC PROPERTIES OF FOODSTUFFS AND TOBACCO USING ONE OR MORE OF SAID PYRANS

This is a division of application Ser. No. 780,684, filed Mar. 23, 1977, now U.S. Pat. No. 4,071,535, which in turn is a division of Ser. No. 676,389, filed 4/12/76, now U.S. Pat. No. 4,071,034.

BACKGROUND OF THE INVENTION

This invention relates to novel 2-alkyl-4-phenyl dihydropyrans and the use thereof in novel foodstuffs and foodstuff flavorings, chewing gums and toothpastes having green, floral, neroli-like, jasmine, peach-lactone-like aromas, and green vegetable-like flavors, processes for augmenting or enhancing neroli-like flavors and grape-like flavors, novel tobacco products, novel tobacco flavoring compositions, and processes for producing same, and has for an object the provision of a composition and process for improving the flavor and aroma of foodstuffs, chewing gums, toothpastes, tobacco and tobacco smoke.

It is well known in the tobacco art that the flavor and aroma of the tobacco product and the smoke from the tobacco are very important considerations insofar as the ultimate consumer is concerned. Considerable efforts have been and are being exerted by the manufacturers of tobacco products to provide a product that will be acceptable to the consumer, particularly as regards flavor and aroma characteristics. It has been the common practice in the tobacco industry to prepare blends of domestic and oriental tobaccos in order to provide smoking tobacco which has a pleasing flavor and aroma before and during smoking. However, such a procedure is costly and may at times become prohibitive in the event that certain types of tobacco may be in short supply. Accordingly, there has been considerable work relating to substances which can be used to impart flavors to various tobacco blends and to augment or enhance flavors of various tobacco blends. These substances are used to supplement natural materials some of which, as stated above, may be in short supply, and to provide more uniform properties to the finished product.

Sweet, spicy, coumarin-like and vanilla-like notes are particularly desirable for many uses concerning the flavoring of tobacco products; both prior to and on smoking.

Schumacher et al., U.S. Pat. No. 3,380,457, issued on Apr. 30, 1958 described an improved tobacco product containing a lactone compound having the generic structure:

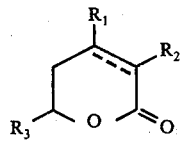

wherein one or more of $R_1$, $R_2$ and $R_3$ are hydrogen or alkyl and wherein the dashed lines represents a single bond or a double bond. Schumacher et al. states that an aroma and flavor which is reminiscent of coconut may be imparted by the use of 3-isopropyl-delta-valerolactone as a tobacco additive; or by the use of 5-hydroxy-3-isopropyl-2-pentenoic acid delta lactone, as a tobacco additive; or a spicy note may be imparted by the use of 5-hydroxy-2-isopropylhexanoic acid delta lactone, as a tobacco additive; or a spicy apple note may be imparted by the use of beta-methyl-delta valerolactone as a tobacco additive.

There has been considerable work performed relating to substances which can be used to impart (or enhance) flavors to (or in) various foodstuffs, chewing gums and toothpastes. These substances are used to diminish natural materials, some of which may be in short supply, and to provide more uniform properties in the finished product. Green, floral, neroli-like, jasmine, peachlactone-like aromas, and green vegetable-like flavors are desirable for many uses in foodstuff flavors, chewing gum flavors and toothpaste flavors as well as the foodstuffs per se, the chewing gums per se and the toothpastes per se.

Dutch published application No. 6,808,496, published on December 19, 1969 (corresponding to British Pat. No. 1,281,813 published on July 19, 1972) discloses, for use in perfumery in order to provide fruity green scents with an overtone of floral muguet, compounds having the generic structure:

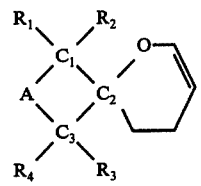

Wherein A together with the carbon atoms $C_1$, $C_2$ and $C_3$, forms a cyclic system which may either by monocyclic or polycyclic, e.g. bicyclic or tricyclic, and may carry one or more alkyl groups on the residue A; and $R_1$ to $R_4$ represents hydrogen atoms or alkyl groups having 1 to 5 carbon atoms with the exception that at least one of $R_1$ to $R_4$ represents an alkyl group when A represents a 1,2-ethylidene or 1,3-propylidene group. More specifically, structures 15, 16, 17, 18, 19, 20, 25 and 26 of the published Dutch Application No. 6,808,496 are as follows:

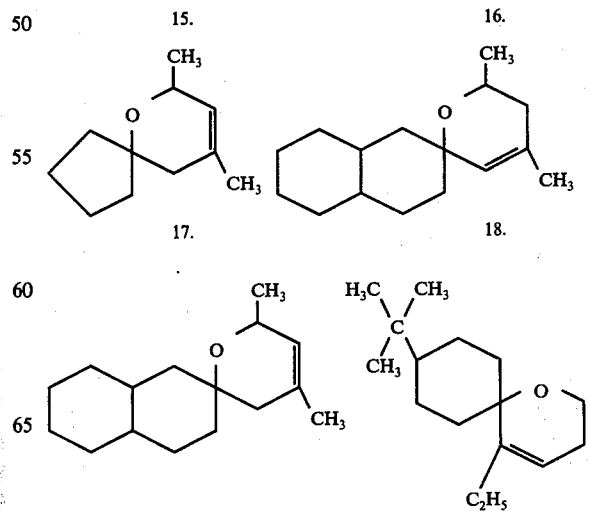

-continued

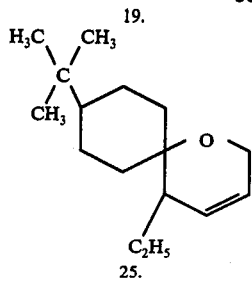
19.

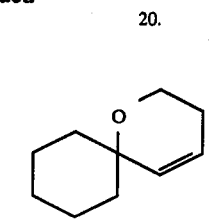
20.

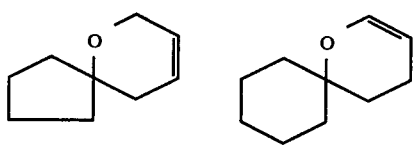
25.   26.

U.S. application for Letters Patent Ser. No. 547,057, filed on Feb. 4, 1975 and assigned to the Assignee of the instant application, International Flavors & Fragrances Inc., discloses methods for preparing foodstuffs, flavoring compositions for foodstuffs, perfume compositions, ingredients for perfume compositions, tobacco compositions and flavoring compositions for tobacco by including therein a pyran derivative (or mixtures thereof) of our invention having the structure:

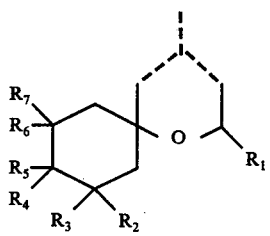

wherein $R_1$ is hydrogen or methyl; wherein $R_2$, $R_3$, $R_4$, $R_5$ $R_6$ and $R_7$ represents hydrogen or $C_1$-$C_5$ lower alkyl; wherein when one of $R_2$, $R_3$, $R_4$, $R_5$, $R_6$ or $R_7$ is any of $C_2$-$C_5$ lower alkyl, each of the other of the $R_2$, $R_3$, $R_4$, $R_5$, $R_6$ and $R_7$ moieties is hydrogen; wherein each of the dashed lines represents a carbon-carbon single bond or a carbon-carbon double bond, with at least one of the dashed lines being a carbon-carbon single bond to produce:

(a) In food flavorings, dill, basil, valerian oil-like, caraway seed-like, thyme-like, piney, raspberry-like, blackberry-like, camphoraceous, herbaceous, eucalyptol-like, cooling, minty, ionone, tea-like, floral, sweet, fruity, woody, apple-like, petitgrain-like, smokey, leafy and green flavor notes.

(b) In perfumes, green, floral, herbal, eucalyptol-like, sweet, minty and terpineol-like notes; and (c) In tobacco flavorings, aromatic, sweet, minty and cooling notes;

foodstuff flavoring compositions, perfume compositions, perfumed articles, tobacco articles and tobacco compositions containing such pyran materials.

The compound 3,6-dihydro-2,4-dimethyl-6-phenyl-2H-pyran having the structure:

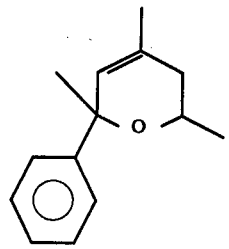

as well as the compound 3,6-dihydro-2,4-dimethyl-6-phenyl-2H-pyran having the structure:

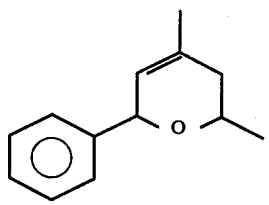

are disclosed by Williams et al., Volume 72, J.Am.-Chem.Soc. 5738-43 (1950) ["A Synthesis of Substituted Pyrans"] specifically at page 5741. However, the organoleptic properties of such compounds are not set forth.

The structures and organolpetic properties of compounds of the prior art are different in kind from the structures and organoleptic properties of the compounds of the instant invention.

THE INVENTION

It has now been discovered that novel foodstuffs, chewing gums, toothpastes, foodstuff flavoring compositions, chewing gum flavoring compositions and toothpaste flavoring compositions having green, floral, neroli-like aromas and neroli-like, green vegetable, jasmine, and peach-lactone-like taste nuances, as well as novel tobacco flavoring compositions, and tobacco products having sweet, spicy, coumarin-like and vanilla-like flavors and aromas prior to and on smoking may be provided by adding to foodstuffs, chewing gums, toothpastes, foodstuff flavors, chewing gum flavors, toothpaste flavors, tobacco flavors and/or tobaccos themselves, one or more pyran derivatives having the structure:

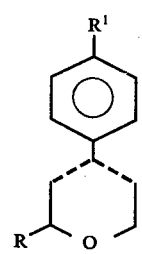

wherein R is one of $C_2$-$C_4$ alkyl, $R^1$ is one of $C_1$-$C_3$ alkyl, and one of the dashed lines is a carbon-carbon double bond and the other of the dashed lines is a carbon-carbon single bond.

Thus, the group exemplified by R are as follows:
ethyl;
n-propyl;
i-propyl;

n-butyl;
i-butyl; and
t-butyl.

It has been found that the tobacco additives of our invention when incorporated into tobacco products impart a flavor and aroma both before and during smoking which many smokers consider to be desirable in smoking products. However, it is pointed out that the methods for defining or characterizing the quality of a flavor or aroma in the tobacco art are almost purely subjective and different smokers may define the same flavor quite differently. The compounds included within the broad scope of this invention may impart flavor or aroma nuances which varies somewhat depending upon the particular alkyl substituents therein. Thus, the compounds comprehended by this invention, by subjective tests, impart characteristic flavors which are desirable in tobacco products and the smoke therefrom even though the exact character thereof cannot be described on the basis of known standards.

In accordance with this invention, one or more of the pyran derivatives of our invention, or mixtures thereof, is added to tobacco or applied to a smoking article or its component parts in amounts of about 50–5000 parts per million (ppm) based on the dry weight of the tobacco product. Preferably, the amount of additive is between about 75 up to 300 ppm by weight in order to provide a tobacco product having a desired flavor and aroma. However, the amount used will depend upon the amount of flavor and aroma desired and the particular compound or mixture thereof that is used. The additive may be incorporated at any step in the treatment of the tobacco but is preferably added after aging, curing and shredding and before the tobacco is formed into cigarettes. Likewise, it will be apparent that only a portion of the tobacco need be treated and the thus treated tobacco may be blended with other tobaccos before the cigarettes or other smoking articles are formed. In such case the tobacco treated may have the additive in excess of the amounts above indicated so that when blended with other tobaccos the final product will have the percentage within the indicated range.

In accordance with one specific embodiment of this invention, an aged, flue-cured and shredded tobacco is sprayed with a 1 percent ethyl alcohol solution of 2-isopropyl-4-phenyldihydropyran in an amount to provide a tobacco containing 100 ppm by weight of the additive on a dry basis. Thereafter, the alcohol is removed by evaporation and the tobacco is manufactured into cigarettes by the usual techniques. It has been found that the cigarette when prepared as indicated has a desired and pleasing flavor, an aroma which to some people is desired as "fruity-coumarin-like" and is detectable and pleasing in the main and side smoke streams when the cigarette is smoked. In addition, the compound promotes salivation, decreases harshness, and enhances the natural tobacco flavor of the tobacco particularly in the main stream. In addition to the "fruity-coumarin-like" note observed, other notes observed are sweet, creamy and "vanilla-like".

The additives falling within the scope of this invention may be applied to the tobacco by spraying, dipping or otherwise, utilizing suitable suspensions or solutions of the additive. Thus water or volatile organic solvents, such as alcohols, diethyl ether, acetone, volatile hydrocarbons and the like, may be used as the carrying medium for the additive while it is being applied to the tobacco. Also, other flavor and aroma producing additives, such as:

(a) Esters for example:
Ethyl butyrate;
Ethyl acetate;
Ethyl valerate;
Amyl acetate;
Phenyl ethyl isovalerate; and
Methyl heptynyl carbonate (b) Aldehydes, for example:
3-phenyl-2-pentenal;
3-phenyl-3-pentenal;
phenyl acetaldehyde;
Cinnamaldehyde; and
Beta-ethyl-cinnamaldehyde (c) Ketones, for example:
Benzylidene acetone;
Acetophenone;
Maltol; and
Ethyl maltol (d) Acetals, for example:
3-phenyl-4-pentenal dimethyl acetal; and
3-phenyl-4-pentenal diethyl acetal
(described in copending application for U.S. Let. Pat. No. 276,922, filed on Aug. 1, 1972).

(e) Natural oils and extracts, for example:
Vanilla;
Coffee extract;
Origanum Oil;
Cocoa Extract;
Oil of Cloves;
Nutmeg Oil;
Celery seed oil;
Bergamot oil; and
Ylang-ylang oil (f) Lactones, for example:
Delta-decalactone;
Delta-undecalactone;
Delta-dodecalactone;
Gamma-undecalactone; and
Coumarin (g) Ethers, for example:
Dibenzyl ether;
Vanillin; and
Eugenol (h) Pyrazines, for example:
2-Acetyl pyrazine;
2-Acetyl-6-methyl pyrazine;
2-Ethyl pyrazine;
2,3-Dimethyl pyrazine;
2,5-Dimethyl pyrazine; and
2-Ethyl-5-methyl pyrazine (i) Pyrroles, for example:
N-cyclopropyl pyrrole; and
N-cyclooctyl pyrrole
as well as those additives disclosed in U.S. Pat. Nos. 2,766,145, 2,905,575, 2,905,576, 2,978,365, 3,041,211, 2,766,149, 2,766,150, 3,589,372, 3,288,146, 3,402,051 and 3,380,457 as well as Australian Pat. Nos. 444,545, 444,507 and 444,389 may be incorporated into the tobacco with the additives of this invention.

While this invention is principally useful in the manufacture of cigarette tobacco, it is also suitable for use in connection with the manufacture of pipe tobacco, cigars or other tobacco products. Furthermore, the compounds may be added to certain tobacco substitute of natural or synthetic origin.

Also, the invention has been particularly described with reference to the addition of the compounds directly to tobacco. However, it will be apparent that the compound of our invention, the pyran derivative, may be applied to the paper of the ciagrette or to the wrapper of a cigar. Also, it may be incorporated into the filter tip, the packaging material or the steam paste employed for gluing the cigarette paper. Thus, a tobacco product is provided which includes the specified additives and tobacco although in every instance the compound need not be admixed with the tobacco as above specifically described.

The compounds of our invention are novel compounds and may be prepared according to the following novel process:

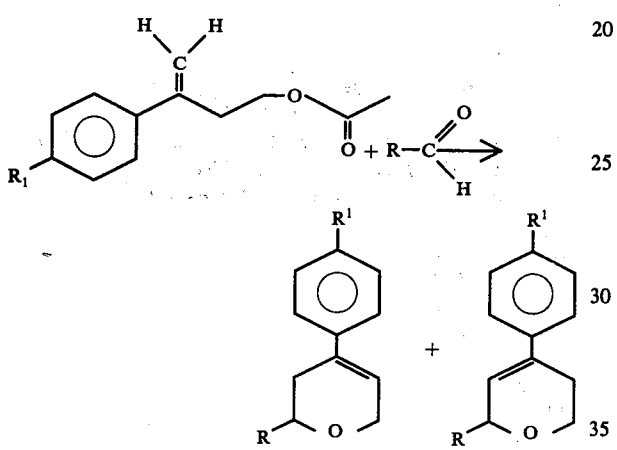

wherein R is one of $C_2$–$C_4$ alkyl, and $R^1$ is one of $C_1$–$C_3$ alkyl. The reaction temperature range is from about 60° C. up to about 120° C. depending on the reactants used and the time of reaction desired.

Thus, for example, the time of reaction is four hours at a temperature of between 66° C. and 85° C., where R is isopropyl and no additional solvent is used.

The foregoing reactions takes place in the presence of a protonic acid catalyst, for example, sulfuric acid, paratoluenes sulfonic acid, phosphoric acid, and benzene sulfonic acid.

When the reaction is completed, the reaction mass is worked-up using standard work-up techniques. Thus, base (e.g. aqueous sodium hydroxide) and inert solvent (e.g. cyclohexane) is added to the reaction mass at the end of the reaction and the organic phase is separated from the aqueous phase, washed, stripped of solvent and fractionally distilled. The fractional distillate may be used "as is" for its organoleptic properties in tobacco or it may be further fractionated whereby the individual chemical components of the mixture are separated; and each component is used for its organoleptic properties. Thus, the instant invention is intended to contemplate not only individual compounds, but mixtures of these compounds as produced by the foregoing reaction.

When the pyran derivatives of our invention having the generic structure:

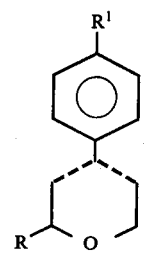

(wherein R is one of $C_2$–$C_4$ alkyl, $R^1$ is one of $C_1$–$C_3$ alkyl, and one of the dashed lines is a carbon-carbon single bond and the other of the dashed lines is carbon-carbon double bond) or mixtures of such compounds are used as food flavor adjuvants, the nature of the co-ingredients included with the said pyran derivatives in formulating the product composition will also serve to alter, augment, modify or enhance the organoleptic characteristics of the ultimate foodstuffs treated therewith. As used herein in regard to flavor, the term "alter" in its various forms means "supply or imparting flavor character or note to otherwise bland, relatively tasteless substance or augmenting or enhancing the existing flavor characteristics where a natural flavor is deficient in some regard or supplementing the existing flavor impression to modify its quality, character or taste".

As used herein the term "foodstuff" includes both solid and liquid ingestible materials which usually do, but need not have nutritional value. Thus, foodstuffs include meats, gravies, soups, convenience foods, beverages, dairy products candies, vegetables, cereals, soft drinks, snacks, chewing gums, chewable vitamin tablets and the like.

As used herein the term "enhance" is intended to mean the intensification of a flavor or aroma characteristic or note without the modification of the quality thereof. Thus, "enhancement" of a flavor or aroma means that the enhancement agent does not add any additional flavor note.

Substances suitable for use herein as co-ingredients or flavoring adjuvants are well known in the art for such, being extensively described in the relative literature. Such adjuvants are required to be non-reactive and organoleptically compatible with the pyrans of our invention. Thus, such adjuvants are required not be deleterious to the overall flavor impact of the foodstuff flavor or other type of flavor to which the pyran derivative (or mixtures thereof) of our invention is intended to be added. Reactivity of such pyran derivative (or mixtures thereof) of our invention with such adjuvant could cause the ultimate product to be deleterious to the overall flavor of the foodstuff to which it is added. Apart from the foregoing requirements another requirement of the adjuvant is that such material being "ingestibly" acceptable and thus non-toxic. Accordingly, such materials which may be in general characterized as flavoring adjuvants or vehicles comprise broadly, stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylate hydroxy anisole (mixture of 2- and 3-tertiary-butyl-4-hydroxy anisole), butylate hydroxy toluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agaragar; carrageenan, cellulose; and cellulose derivatives such as carboxymethyl cellulose and methyl cellulose; natural and synthetic gums such as gum arabic, gum tragacanth; gelatin, proteinaceous materials, lipids; carbohydrates; starches pectins, and emulsifiers, e.g., mono-and diglycerides of fatty acids, skim milk powder, hexoses, pentoses, disaccharides, e.g., sucrose, corn syrup solids and the like.

Surface active agents include emulsifying agents, e.g., fatty acids such as capric acid, caprylic acid, palmitic acid, myristic acid and the like, mono-and diglycerides of fatty acids, lecithin, defoaming and flavor-dispersing agents such as sorbitan mono-stearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcumin and the like, firming agents such as aluminum sodium sulfate, calcium chloride and calcium gluconate; texturizers; anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources, such as zinc chloride, zinc sulfate and the like.

Other flavorants and flavor intensifiers include organic acid, e.g., fatty saturated acids, unsaturated acids and amino acids; alcohols, e.g., primary and secondary alcohols, esters, carbonyl compounds, e.g., aldehydes and ketones as well as lactones; cyclic organic materials including benzene derivatives, isocyclics, heterocyclics such as furans particularly 2,5-dimethyl-3-acetyl furan and 2-methyl-2,3-dihydro furan-3-one, pyridines, pyrazines (particularly monoalkyl, dialkyl, trialkyl and tetraalkyl substituted pyrazines) and the like, sulfur-containing materials including thiazoles, disulfides, thiols, sulfides, aldehydes (for example, 3-phenyl-4-pentenal, 3-phenyl-3-pentenal, 3-phenyl-2-pentenal, 2-phenyl-2-pentenal and 2-phenyl-3-methyl-2-butenal); tri-sulfides and the like; other flavor potentiators such as monosodium glutamate, guanylates, inosinates, natural and synthetic flavorants such as vanillin, ethyl vanillin, diacetyl, phenethyl-2-furoate, maltol, natural gums and the like; spices, herbs, essential oils and extractives including "bitterness principles" such as theobromine, caffeine, naringin and other suitable materials creating a bitter effect.

The specific flavoring adjuvant selected for use may be either solid or liquid depending upon the desired physical form of the ultimate product, e.g., foodstuff, whether simulated or natural, and should, in any event, be capable of providing an environment in which the pyran derivative of our invention (or mixtures thereof) can be dispersed or admixed to provide a homogeneous medium. In addition, selection of one or more flavoring adjuvants as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of pyran derivative (or mixtures thereof) of our invention employed in a particular instance can vary over a relatively wide range whereby various organoleptic effects are created. All parts and percentages given herein are by weight unless otherwise specified. Thus, correspondingly, greater amounts would be necessary in those instances wherein the ultimate food composition to be flavored is relatively bland to the taste, whereas relatively minor quantities may suffice for purposes of enhancing the composition merely deficient in some natural flavor nuance or aroma nuance. Thus, the primary requirement is that the amount selected to be effective, e.g., sufficient to alter the organoleptic characteristics of the parent composition, whether foodstuff per se or flavoring composition. Thus, the use of insufficient quantities of pyran derivative (or mixtures thereof) will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded as significant in the content of the present invention consistent with the obtention of desired flavoring effects.

Thus, and with respect to ultimate food compositions it has been found that quantities of pyran derivative (or mixtures thereof) of our invention, ranging from a small but effective amount, e.g., 0.2 parts per million up to about 200 parts by million by weight based on total composition are suitable. Concentrations in excess of the maximum quantity stated are not normally recommended since they fail to provide commensurate enhancement or augmentation of the organoleptic properties. In those cases, wherein the pyran derivative (or mixtures thereof) of our invention is added to the foodstuff as an integral component of the flavoring composition, it is, of course, essential that the total quantity of flavoring composition employed be sufficient to yield an effective pyran derivative (or mixtures thereof) concentration in the foodstuff product.

Food flavoring compositions prepared in accordance with the present invention preferably contain the pyran derivative (or mixtures thereof) in concentrations ranging from about 0.2% up to about 10% by weight based on the total weight of said flavoring composition.

The compositions described herein can be prepared according to conventional techniques well know as typified by cake batters and fruit juices and vegetable juices and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by admixing the pyran derivative (or mixtures thereof) of our invention with, for example, gum arabic, gum tragacanth, carrageenan and the like and thereafter spray-drying the resultant mixture whereby to obtain the particulate solid product. Pre-prepared flavor mixes in powder form, e.g, a grape flavored powder (for producing a gelatin desert for example) obtained by mixing dried solid components, e.g., starch, sugar, and the like and one or more of the pyran derivative (or mixtures thereof) of our invention in a dry blender until the requisite degree of uniformity is achieved.

It is presently preferred to combine one or more of the pyran derivative (or mixtures thereof) of our invention with at least one of the following adjuvants:

Natural orange oil;
Methional;
Rum ether;
Diethyl malonate;
Ethyl propionate;
Amyl isovalerate;
Acetic acid;
Ethyl nonanoate;
Phenyl ethyl acetate;
Isobutyl formate;
Methyl anthranilate;
Ethyl heptanonate;
Cinnamyl propionate;
Ethyl acetate;
Ethyl butyrate;
Cinnamyl alcohol;
Cinnamyl isovalerate;
Cinnamyl propionate;
Citral;
Ethyl benzoate;
Ethyl caproate;
Ethyl methylphenylglycidate;
Ethyl oenanthate;
Ethyl pelargonate;
Hydroxy citronellal;
Petitgrain oil;
Terpinenyl acetate;
Tolualdehyde;
Methyl naphthyl ketone;
Benzylidene acetone,
Alpha ionone,
Lemon essential oil; and
Lime essential oil.

The following examples are given to illustrate the embodiments of the invention as it is presently preferred to practice it. It will be understood that these examples are illustrative and the invention is to be considered as restricted thereto except as indicated in the appended claims.

EXAMPLE I

PREPARATION OF 2-ISOPROPYL-4-PHENYL-DIHYDROPYRAN

Reaction:

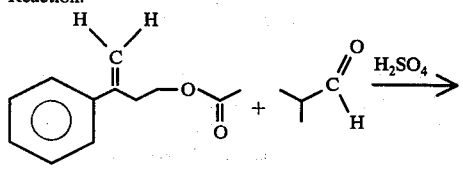

-continued

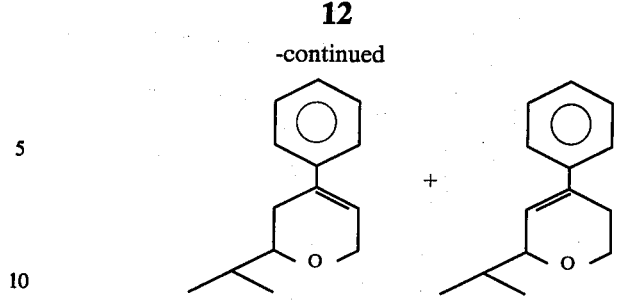

In a 500 ml three neck reaction flask equipped with stirrer, thermometer, reflux condenser and addition funnel is placed 72 gms (1 mole) of isobutyl aldehyde. The isobutyl aldehyde is heated to 66° C. (reflux) and from the additional funnel, over a period of 1 hour, is added a mixture of 204 g (1 mole) of 3-phenyl-3-buten-1-yl acetate and 1 g concentrated sulfuric acid. During addition of the 3-phenyl-3-buten-1-yl acetate/sulfuric acid mixture, the reaction mass temperature increases to 80°–85° C. At the end of the addition of the mixture, the reaction mass is stirred for a period of three hours at 80°–85° C. The reaction mass is then cooled to room temperature and 100 ml of a 10% aqueous sodium hydroxide solution is added thereto with stirring, followed by 100 ml cyclohexane. The resulting mixture is transferred to a separatory funnel and the aqueous layer is removed. The organic layer is then washed with one 100 ml portion of 10% aqueous sodium chloride. The organic layer is then stripped of solvent and rushed over. To the rushed over material 4.5 gms Primol®, 0.5 gms triethanolamine and 0.1 gms of Ionox® is added. The resulting material is then distilled in an 8 plate vigreux column yielding the following fractions:

| Fraction No. | Vapor Temp.(° C) | Liquid Temp.(° C) | Pressure (mm Hg) | Weight of Fraction (gram) | Reflux Ratio |
|---|---|---|---|---|---|
| 1 | 67–103° C | 136–137° C | 3.4–3.6 | 5.8 | 20:1 |
| 2 | 107 | 141 | 3.4 | 9.4 | 20:1 |
| 3 | 109 | 145 | 3.5 | 15.1 | 20:1 |
| 4 | 112 | 147 | 3.5 | 12.7 | 20:1 |
| 5 | 125 | 154 | 3.5 | 8.9 | 20:1 |
| 6 | 125 | 155 | 3.5 | 14.5 | 20:1 |
| 7 | 129 | 156 | 3.5 | 11.9 | 9:1 |
| 8 | 130 | 160 | 3.5 | 14.6 | 9:1 |
| 9 | 132 | 170 | 3.5 | 14.9 | 9:1 |
| 10 | 150 | 195 | 3.5 | 9.5 | 9:1 |
| 11 | 159 | 200 | 3.5 | 11.8 | 9:1 |
| 12 | 162 | 205 | 3.5 | 9.2 | 9:1 |
| 13 | 160 | 208 | 3.5 | 6.5 | 9:1 |

Fractions 7–10 are bulked and these fractions have a sweet, spicy, coumarin-like aroma, which causes the reaction product to be useful in augmenting or enhancing the flavor of tobacco.

Infra-red analysis, NMR analysis and Mass Spectral analysis yield the information that the resulting material is a mixture of compound having the structures:

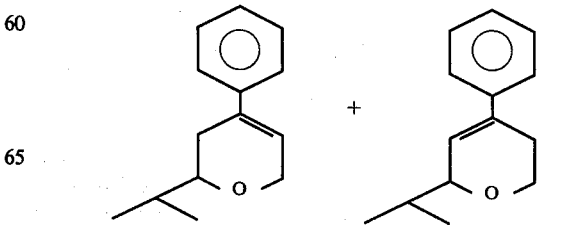

These compounds are separated using preparative GLC separation techniques.

Fraction 7 contains the compounds having the structure:

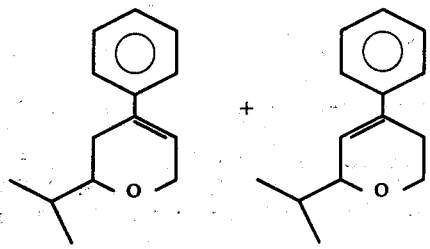

The Mass Spectral analysis is as follows:

| m/e | Relative Intensity |
|---|---|
| 43 | 34 |
| 77 | 28 |
| 91 | 49[4] |
| 115 | 53[3] |
| 118 | 55[2] |
| 128 | 35 |
| 129 | 40[6] |
| 131 | 45[5] |
| 159 | 100[1] |
| m202 | 36 |

The NMR analysis for Fraction 7 is as follows:

| NMR Analysis | Interpretation |
|---|---|
| 0.78 ppm | Methyl protons |
| 1.78 | Me₂CH— (Me, Me, H, C—) |
| 2.30 | φ—H—C |
| 3.24 | —H—O—C |
| 3.68 | —CH₂—O— |
| 4.02 | =C—CH₂—O— |
| 4.32 | =C—C—O— (H) |
| 6.04 | olefinic proton |
| 7.30 ppm | aromatic protons |

FIG. 1 is the NMR spectrum for Fraction 7.

The IR analysis is as follows: 680cm⁻¹, 740, 1070, 1120, 1140, 1360, 1380, 1440, 1590, 2920, 2950.

Figure 2:
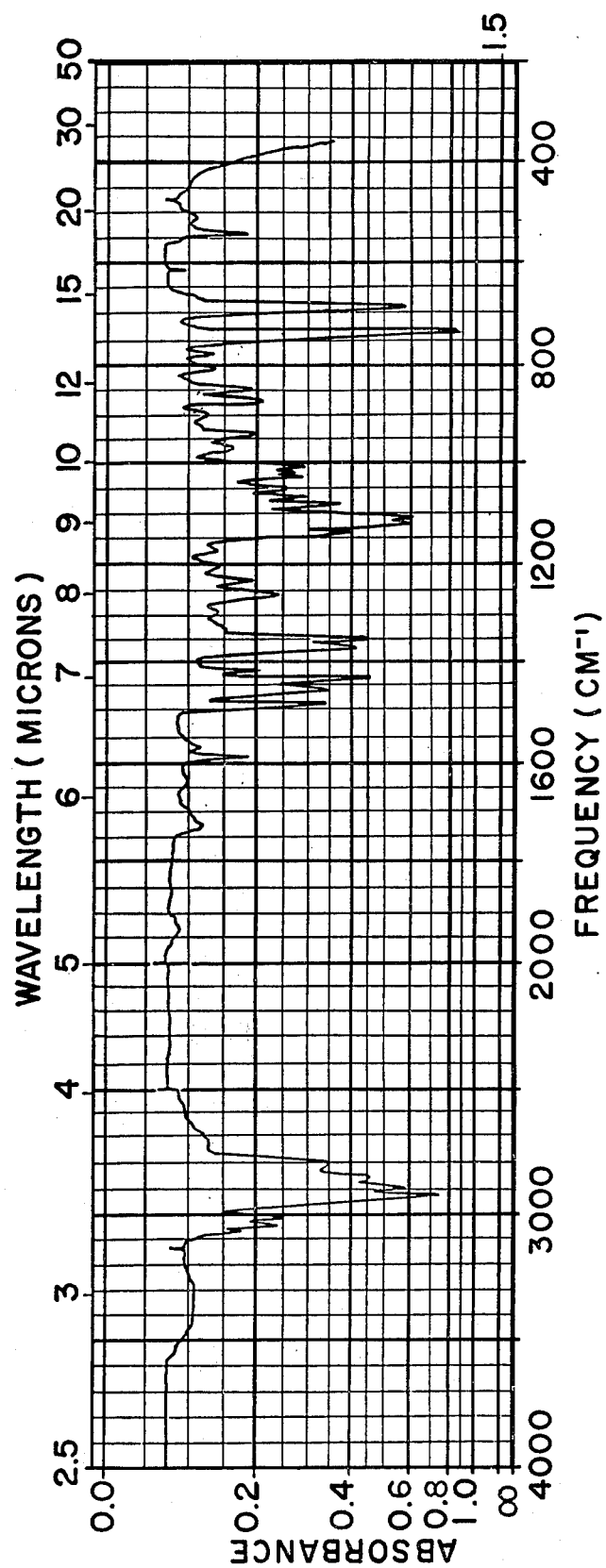

FIG. 2 is the infra-red spectrum for Fraction 7.

EXAMPLE II

PREPARATION OF 2,4-DIMETHYL-2-PHENYL-DIHYDROPYRAN

Reaction:

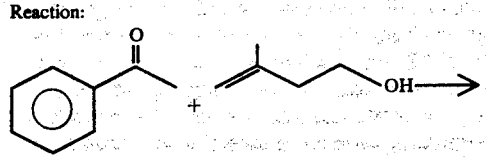

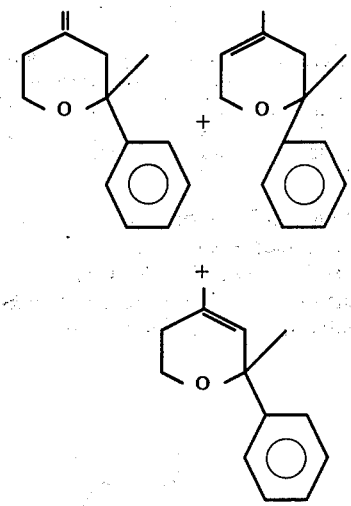

Into a one-liter three neck flask equipped with stirrer, condenser, Barrett Trap, thermometer, addition funnel and heating mantle is placed 288 gms (2.4 moles) of acetophenone, 150 ml cyclohexane, 1 g of concentrated sulfuric acid and 1 g of Ionol ®. The resulting mixture is heated to reflux temperature (94° C.). Then 208 gms (2.4 moles) of 3-methyl-3-buten-1-ol is added, dropwise from the addition funnel, to the reaction mass with stirring while maintaining the reaction mass at reflux. Water of reaction formed is azeotroped over into the Barrett Trap. The reaction mass is heated for a period of 10 hours, during which time 24 ml water collected. At the end of the 10 hour period, the reaction is cooled to room temperature and 2 gms of a 50% sodium hydroxide solution are added. The reaction mass is then rushed over using a 2 inch splash column after adding thereto 10 gms Primol ® and 0.1 gms Ionol ®. Fractions collected and fractionation data for this rush over is as follows:

| Fraction No. | Vapor Temp.(° C) | Liquid Temp. (° C) | Pressure (mm Hg) | Weight of Fraction(gram) |
|---|---|---|---|---|
| 1 | 23–31° C | 30–110° C | 100.0–10-0.0 | 88.9 |
| 2 | 71 | 75 | 4.5 | 59.0 |
| 3 | 66 | 84 | 2.9 | 231.4 |
| 4 | 78 | 107 | 2.5 | 40 |
| 5 | 100 | 129 | 2.5 | 29.6 |
| 6 | 147 | 177 | 2.7 | 32.3 |
| 7 | 160 | 202 | 2.7 | 18.8 |

Fractions 4–6 from the rush over distillation are bulked and redistilled on an 8 plate vigreux column, after adding thereto 4.5 gms Primol ®, 0.1 gms Ionox ®, and 0.5 triethanolamine. Fractionation data for the distillation using the 8 plate vigreux column is as follows:

| Fraction No. | Vapor Temp. (° C) | Liquid Temp. (° C) | Pressure (mm Hg) | Weight of Fraction (gram) | Reflux Ratio |
|---|---|---|---|---|---|
| 1 | 58–60° C | 80–83° C | 3.2–3.1 | 7.5 | 20:1 |
| 2 | 60 | 89 | 3.3 | 8.9 | 20:1 |
| 3 | 64 | 103 | 3.2 | 7.9 | 20:1 |
| 4 | 84 | 108 | 3.3 | 5.8 | 20.1 |
| 5 | 94 | 114 | 3.5 | 11.9 | 20.1 |
| 6 | 98 | 120 | 3.6 | 9.8 | 20.1 |
| 7 | 104 | 136 | 3.6 | 12.4 | 20.1 |
| 8 | 106 | 142 | 3.5 | 12.2 | 20.1 |
| 9 | 109 | 151 | 3.5 | 8.6 | 20.1 |

-continued

| Fraction No. | Vapor Temp. (° C) | Liquid Temp. (° C) | Pressure (mm Hg) | Weight of Fraction (gram) | Reflux Ratio |
|---|---|---|---|---|---|
| 10 | 118 | 169 | 3.5 | 5.2 | 20.1 |
| 11 | 124 | 192 | 3.5 | 4.3 | 20.1 |
| 12 | 138 | 207 | 3.5 | 3.6 | 20.1 |

Fraction 7 is subjected to GLC analysis (condition: 10′ × ¼ inches carbowax column operated at 180° C.). GLC, NMR, Mass Spectral and IR analyses yield the information that Fraction 7 consists essentially of a mixture of compounds having the structures:

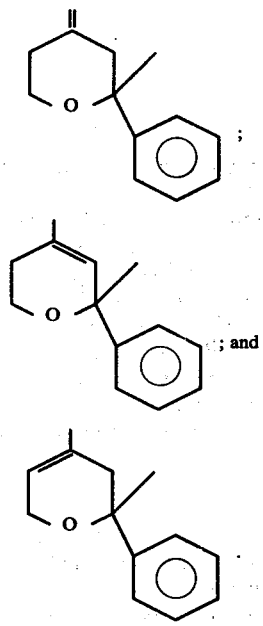

The Mass Spectral analysis is as follows:

| m/e | Relative Intensity |
|---|---|
| 43 | 100[1] |
| 67 | 54[6] |
| 68 | 78[3] |
| 69 | 22 |
| 77 | 38 |
| 105 | 65[5] |
| 121 | 63[5] |
| 160 | 27 |
| 173 | 92[2] |
| m188 | 25 |

The NMR analysis for the resulting mixture is as follows:

| NMR Analysis | Interpretation |
|---|---|
| 7.30 ppm | Aromatic protons |
| 5.80 | Olefinic proton (cyclic) |
| 5.30 | Olefinic proton (cyclic) |
| 4.78 | $>C=CH_2$ |
| 4.22–3.35 | $HC-O-$ + $-CH_2-O-$ |
| 2.32 | $-CH_2-$ |
| 1.80 | $=C-CH_3$ |
| 1.50 | $CH_3-\overset{O}{\underset{|}{C}}-\bigcirc$ |
| 1.20 | Impurity |

Figure 3:
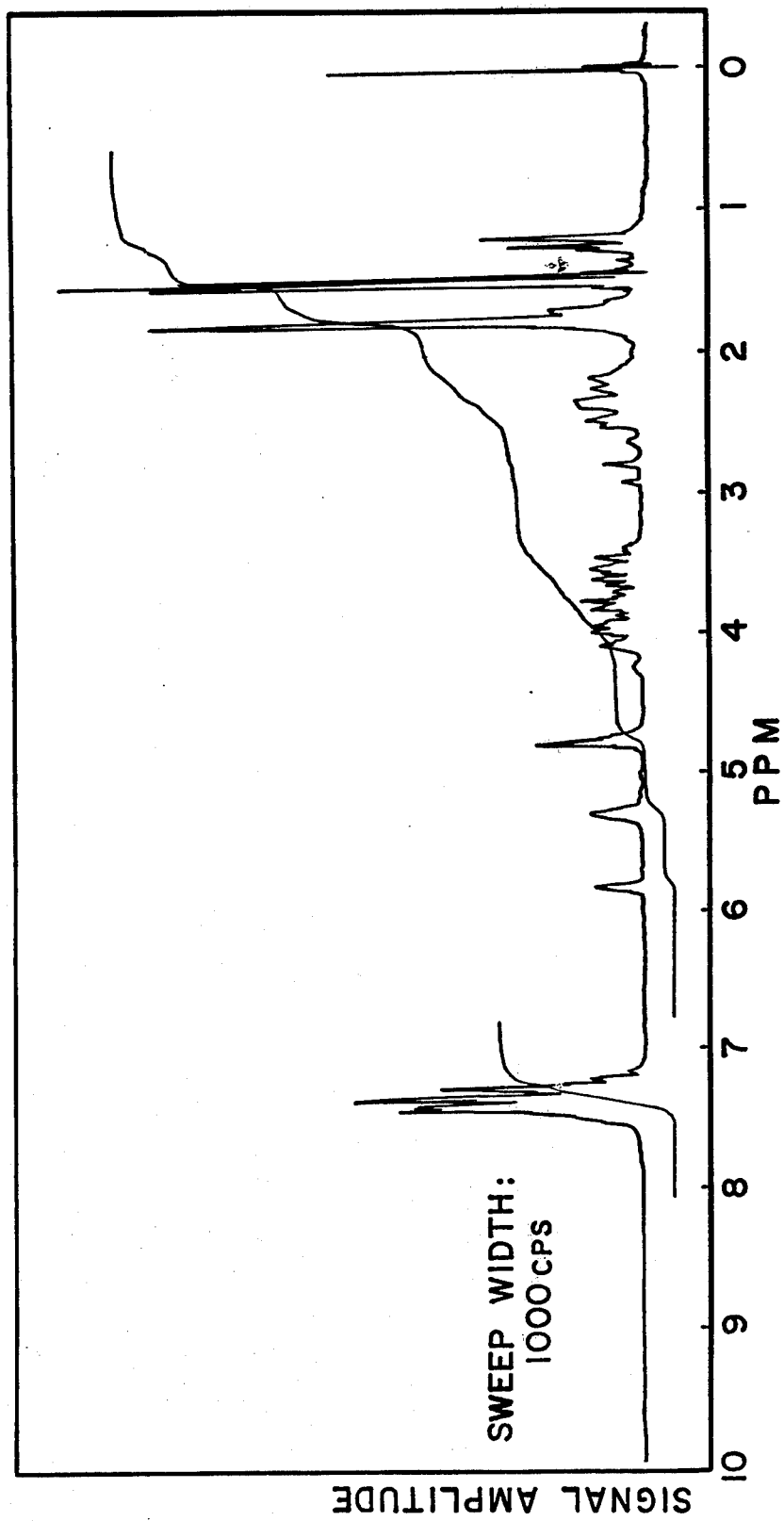

The NMR Spectrum for Fraction 7 is set forth in FIG. 3.

The infra-red analysis for Fraction 7 is as follows: 690cm⁻¹, 760, 1070, 1080, 1120, 1360, 1440, 2850, 2920.

The infra-red spectrum for Fraction 7 is set forth in FIG. 4.

Fraction 7 is not considered to be suitable for tobacco having a green, fatty, herbaceous and slightly cooling affect insofar as its aroma is concerned and having a green, floral, herbaceous, spicy, parsely-like aroma on dry out.

Insofar as its use in perfumery is concerned, this material has a sweet, green, floral, spicy aroma with a hay (acetophenone-like) nutmeg character with spicy, green, floral and citrusy undertones. On dry out this material becomes nutmeg-like.

Insofar as its flavor properties are concerned, Fraction 7 has a fatty, ivy-green, green aroma and a sweet, fatty, green, ivy-green and astringent flavor. It is not considered to have utility for flavor work.

EXAMPLE III

USE OF 2-ISOPROPYL-4-PHENYL-DIHYDROPYRAN IN TOBACCO

The following tobacco flavor formulation (A) is prepared:

| Ingredients | Parts by Weight |
|---|---|
| Ethyl Butyrate | 0.05 |
| Ethyl Valerate | 0.05 |
| Maltol | 2.00 |
| Cocoa Extract | 26.00 |
| Coffee Extract | 10.00 |
| Ethanol (95% aqueous) | 20.00 |
| Water | 41.90 |

A tobacco formulation (B) is prepared as follows:

| Ingredients | Parts by Weight |
|---|---|
| Bright Tobacco | 40.1 |
| Burley Tobacco | 24.9 |
| Maryland Tobacco | 1.1 |
| Turkish Tobacco | 11.6 |
| Stem (Flue-cured) Tobacco | 14.2 |
| Glycerine | 2.8 |
| Water | 5.3 |

The flavor formulation (A) is added to a portion of the smoking tobacco formulation (B) at the rate of 0.1 percent by weight of the tobacco. The flavored and nonflavored tobacco formulations are then formulated into cigarettes by the usual manufacturing procedures:

(i) At the rate of 100 ppm to one-fourth of the cigarettes in each group is added 2-isopropyl-4-phenyl-dihydropyran (bulked Fractions 7–10, produced according to Example I). The use of the 2-isopropyl-4-phenyl-dihydropyran in the cigarettes causes the cigarettes prior to smoking to have a sweet, spicy, coumarin-like aroma. In smoke flavor, in the main stream, the use of the 2-isopropyl-4-phenyl-dihydro-2H-pyran promotes salivation, decreases harshness and has a sweet, creamy, vanilla and coumarin-like effect; and also enhances the natural tobacco-like character. In the side stream, the same effects are observed.

(ii) At the rate of 200 ppm to one-fourth of the cigarettes in each group is added 2-isopropyl-4-phenyl-dihydropyran (bulked Fractions 7-10, produced according to Example I). The use of the 2-isopropyl-4-phenyl-dihydropyran in the cigarettes causes the cigarettes prior to smoking to have a sweet, spicy, coumarin-like aroma. In smoke flavor, in the main stream, the use of the 2-isopropyl-4-phenyl-dihydro-2H-pyran promotes salivation, decreases harshness and has a sweet, creamy, vanilla and coumarin-like effect; and also enhances the natural tobacco-like character. In the side stream, the same effects are observed.

One-fourth of the cigarettes remains totally without added flavorants. One-fourth of the cigarettes contain only formulation (A) added thereto; but no 2-isopropyl-4-phenyl-dihydro-2H-pyran.

In general, on smoking, the cigarettes containing the exemplified 2-isopropyl-4-phenyl-dihydro-2H-pyran have a sweet, creamy, vanilla and coumarin-like aroma which enhances the natural tobacco character, decreases harshness and promotes salivation and is in general more desirable than those cigarettes not containing this pyran whether or not the ingredients of formulation (A) are included in the tobacco.

EXAMPLE IV

USE IN FOODSTUFF FLAVORS OF 2-ISOPROPYL-4-PHENYL-2H-DIHYDROPYRAN

The following basic concord grape flavor formulation is prepared:

| Ingredients | Parts by Weight |
|---|---|
| Methional (10% in 95% food grade aqueous ethanol) | 10 |
| Rum ether | 10 |
| Diethyl malonate | 15 |
| Ethyl propionate | 40 |
| Amyl isovalerate | 40 |
| Glacial acetic acid | 40 |
| Fusel Oil | 35 |
| Ethyl nonanoate | 40 |
| Phenyl ethyl acetate | 50 |
| Isobutyl formate | 50 |
| Methyl anthranilate | 100 |
| Ethyl heptanoate | 60 |
| Cinnamyl propionate | 120 |
| Ethyl acetate | 200 |
| Ethyl butyrate | 190 |

The foregoing formulation is split into two parts. To the first part, at the rate of 2% by weight is added 2-isopropyl-4-phenyl-2H-dihydropyran. To the second portion of the formulation nothing additional is added thereto. Both formulations are compared at the rate of 50 ppm in water. The flavor formulation containing the 2-isopropyl-4-phenyl-2H-dihydropyran has more of the delicate aroma and taste characteristics of fresh concord grapes; and a fuller, more natural concord grape juice taste. The 2-isopropyl-4-phenyl-2H-dihydropyran improves the grape flavor and it is therefore preferred over the grape flavor that does not contain the said 2-isopropyl-4-phenyl-2H-dihydropyran.

EXAMPLE V

USE OF 2-ISOPROPYL-4-PHENYL-2H-DIHYDROPYRAN IN ORANGE JUICE 2-isopropyl-4-phenyl-2H-dihydropyran produced according to the process of Example I is added to canned, unsweetened orange juice at the rate of 5 ppm. This compound adds a pleasant orange flavor-like aroma, improves the cooked orange juice taste and makes the juice fresher, fruitier and is therefore more preferred.

What is claimed is:

1. A process for preparing one or more chemical compounds having the generic structure:

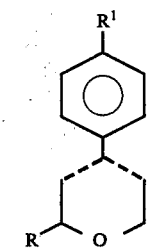

wherein one of the dashed lines is a carbon-carbon double bond and the other of the dashed lines is a carbon-carbon single bond and R is one of $C_2$-$C_4$ alkyl and $R^1$ is one of $C_1$-$C_3$ alkyl comprising admixing in the presence of a protonic acid catalyst at a temperature in the range of from about 60° C. up to about 120° C. the compounds having the structures:

wherein R is one of $C_2$-$C_4$ alkyl and $R^1$ is one of $C_1$-$C_3$ alkyl.